(12) United States Patent
Heinemann et al.

(10) Patent No.: US 9,265,861 B2
(45) Date of Patent: Feb. 23, 2016

(54) COMPOSITE MATERIAL CONSISTING OF A COLLAGEN MATRIX MINERALISED WITH SILICATE AND CALCIUM PHOSPHATE PHASES, METHOD FOR THE PRODUCTION AND USE THEREOF

(75) Inventors: Sascha Heinemann, Dresden (DE); Hartmut Worch, Dresden (DE); Thomas Hanke, Berlin (DE)

(73) Assignee: Technische Universität Dresden, Dresden (DE)

( * ) Notice: Subject to any disclaimer, the term of this patent is extended or adjusted under 35 U.S.C. 154(b) by 532 days.

(21) Appl. No.: 13/063,469

(22) PCT Filed: Sep. 11, 2009

(86) PCT No.: PCT/EP2009/061809
§ 371 (c)(1),
(2), (4) Date: Jun. 1, 2011

(87) PCT Pub. No.: WO2010/029150
PCT Pub. Date: Mar. 18, 2010

(65) Prior Publication Data
US 2011/0237552 A1  Sep. 29, 2011

(30) Foreign Application Priority Data
Sep. 11, 2008 (DE) .......................... 10 2008 047 405

(51) Int. Cl.
| | | |
|---|---|---|
| *A61K 9/14* | (2006.01) | |
| *A61L 27/52* | (2006.01) | |
| *A61L 27/34* | (2006.01) | |
| *A61L 27/44* | (2006.01) | |
| *A61L 27/46* | (2006.01) | |

(52) U.S. Cl.
CPC .................. *A61L 27/52* (2013.01); *A61L 27/34* (2013.01); *A61L 27/446* (2013.01); *A61L 27/46* (2013.01); *A61L 2420/04* (2013.01)

(58) Field of Classification Search
None
See application file for complete search history.

(56) References Cited

U.S. PATENT DOCUMENTS

2007/0196419 A1* 8/2007 Teller et al. .................... 424/423
2008/0147197 A1* 6/2008 McKay ...................... 623/23.51

FOREIGN PATENT DOCUMENTS

| DE | 198 11 600 | 9/1999 |
|---|---|---|
| DE | 199 62 090 | 6/2000 |
| DE | 10 2004 012 411 | 9/2005 |
| DE | 10 2006 014 522 | 10/2007 |
| WO | 2005/099785 | 10/2005 |
| WO | 2008/023025 | 2/2008 |

OTHER PUBLICATIONS

Bradt et al (Chem Mater 11:2694-2701, 1999).*
Koken, FAQ Collagen (available online at www.kokenmpc.co.jp as of 2005).*
Ehrlich H. et al.: Demineralization of natural silica based biomaterials: new strategy for the isolation of organic frameworks; BIOmaterialien 6 (2005) No. 4, pp. 297-302; (mentioned in instant specification; p. 2, 3rd paragraph).
Ehrlich H. et al.: A Modern Approach to Demineralization of Spicules in Glass Sponges (Porifera: *Hexactinellida*) for the Purpose of Extraction and Examination of the Protein Matrix; Russ Marin Biol 32 (2006) No. 3, pp. 186-193; (mentioned in instant specification; p. 2, 3rd paragraph).
Max Plank Forschung (Ed.): Knochen auf den Zahn gefühlt; Forschung aktuell, vol. 1 (2005) pp. 10-11 (mentioned in instant specification; paragraph bridging pp. 2-3), Considered to the extent of Applicant's summary.
Wolf C. et al.: Influence of artificial extracellular matrices on Ti6A14V implants on binding and release of VEGF, Abstracts International Symposium, Interface Biology of Implants, Rostock, Germany, May 14-16 2003, BIOmaterialien 4: 158 (2003); (mentioned in instant specification; paragraph bridging pp. 7-8).
Wolf-Brandstetter C. et al.: Influence of Modified Extracellular Matrices on Ti6A14V implants on binding and release of VEGF; J. Biomed. Mat. Res A. 79: 882-894 (2006); (mentioned in instant specification, paragraph bridging pp. 7-8).
Worch H. et al.: Innovative Materialsysteme für die Funktionalisierung von Implantaten und den Gewebeaufbau in der Implantologies; BMBF Project 03N0415/9 (Oct. 1999 to Oct. 2002); Collection Deutsche Forschungsberichte TIB/UB Hannover; Germany; (mentioned in instant specification, paragraph bridging pp. 7-8), Considered to the extent of Applicant's summary.
Heinemann S. et al.: Bioactive silica-collagen composite xerogels modified by calcium phosphate phases with adjustable mechanical properties for bone replacement; Acta Biomaterialia 5 (2009) 1979-1990.

* cited by examiner

*Primary Examiner* — Craig Ricci
(74) *Attorney, Agent, or Firm* — Gudrun E. Huckett

(57) ABSTRACT

The invention relates to novel composite materials based on a collagen matrix mineralized with silicate and calcium phosphate phases, to a method for the production thereof and use thereof as an implant material which can be shaped in a plurality of ways, a biological coating or active substance carrier. The claimed composite material comprises a collagen matrix which is mineralized with silicate and a calcium phosphate phase, said collagen being a recombinate collagen, collagen from Eumetazoa, sponge collagen from a sponge of the Demospongia class (horn sponges) or Calcarea (calcareous sponges), a synthetic collage analog, a collagen derivative or a mixture of said collagens.

10 Claims, 4 Drawing Sheets a)

b)

COMPOSITE MATERIAL CONSISTING OF A COLLAGEN MATRIX MINERALISED WITH SILICATE AND CALCIUM PHOSPHATE PHASES, METHOD FOR THE PRODUCTION AND USE THEREOF

BACKGROUND OF THE INVENTION

The invention concerns novel composite materials on the basis of a collagen matrix mineralized with silicate and calcium phosphate phases, method for their production as well as their use as implant material designable in a plurality of ways, biologizing coating, or active ingredient carrier.

The development of novel biomaterials is driven mainly by the desire to produce technically mature tissue and bone implants for medical applications. Depending on the implantation site and function, special demands with regard to bioactivity, biocompatibility, and mechanical strength are put on them. Generally, these demands can be hardly fulfilled by single component materials. Biological components that, for functional reasons, are usually considered a prerequisite have often an excellent biocompatibility but are not capable of withstanding great mechanical loads. For this reason, strategies for reinforming such materials are being worked on increasingly. For example, this would be achievable by combining further inorganic non-metallic components that can absorb the corresponding loads but, in turn, must have satisfactory biocompatibility.

SUMMARY OF THE INVENTION

Bioactivity is to be understood as the property of a material in environments of (simulated) body fluid to promote the formation of an apatite layer on its surface. Especially in the field of bone replacement materials a bioactivity as high as possible is required in order to produce a force-fit connection between implant and recipient tissue. Materials on the basis of collagen are of especially great interest for biomedical applications. As body-own structural protein collagen is present ubiquitously in all multicellular animals and is, with approximately one-third of the entire protein mass, their most common protein. It is nearly non-toxic, bio-resorbable and hardly immunogenic so that an excellent biocompatibility results. As a starting material for industrial applications, usually collagen of the type I is used that is obtained, for example, from tendons, cartilage and skins of cows, calves, and pigs. By now, numerous products on the basis of collagen have been developed and established in many areas of cosmetics and medicine. Further applications are prevented however because of the limiting mechanical properties of pure collagen products.

In the animal kingdom, evolution has impressively overcome this deficit in that load-bearing elements of an organism are built of material composites. The present application combines the basic principles of natural examples, i.e., spicules of marine glass sponges and mammalian bone.

The inventors have proven that already the marine glass sponges of 600 million years of age are an example of naturally occurring composite materials. [Ehrlich, H., Hanke, T., Simon, P., Goebel, C, Heinemann, S., Born, R., Worch, H.: Demineralization of natural silica based biomaterials: new strategy for the isolation of organic frameworks. In: BIOmaterialien 6 (2005), No. 4, pp. 297-302; Ehrlich, H., Ereskovskii, A. V., Drozdov, A. L., Krylova, D. D., Hanke, T., Meissner, H., Heinemann, S., Worch, H.: A Modern Approach to Demineralization of Spicules in Glass Sponges (Porifera: Hexactinellida) for the Purpose of Extraction and Examination of the Protein Matrix. In: Russ Marin Biol 32 (2006), No. 3, pp. 186-93]. Modern analytical methods disclosed that the spicules of the marine glass sponge *Hyalonema sieboldi* are comprised of a silicated collagen matrix which is the basis for their special mechanical properties.

In addition to other functions, mammalian bone must withstand as a support element within the body various mechanical loads [Wintermantel, E., Ha, S.-W.: Biokompatible Werkstoffe and Bauweisen; Springer Verlag, 1998]. Despite a high strength (compressive stress), it must however also have a certain elasticity so that, under unfavorable load conditions (leverage), it will not experience brittle fracture. These requirements are fulfilled by the bone by its hierarchical construction and especially decisively by its material composition at the molecular level. The organic bone matrix that constitutes approximately 30% of the bone is comprised of approximately 95% of collagen that takes on the role of the elastic component for absorbing tension and bending stress. In the course of a mineralization process, between the collagen fibrils mineral calcium phosphate (primarily hydroxyl apatite) in the form of crystalline platelets of a thickness of approximately two to four nanometers are deposited [chapter Forschung aktuell. In: MaxPlankForschung (Ed.): Knochen auf den Zahn gefühlt; Vol. 1. 2005, pp. 10-1].

Depending on the level of mineralization (approximately 65% in bone) the flexible basic frame of collagen is mechanically reinforced so that the strength, primarily under compressive loading, is enormously increased. Based on such knowledge, possibilities for imitating naturally occurring composite materials—primarily that of bone—have been worked on intensively for some time, however, only with very limited success.

In patent application WO 2008/023025, PCT/EP2007/058694, the inventors describe a method for producing hybrid materials based on a silicated collagen matrix. It is based on a sol-gel process in which silicic acid molecules polymerize under certain conditions to silicate nanoparticles. When this process is carried out in the presence of collagen fibrils, the polymerization preferably takes place at the fibrils. For a suitable composition a hybrid hydrogel can be produced in this way. The latter can be dried under certain conditions and can be converted into a hybrid xerogel. Since the solids component of the hydrogel is however very minimal as a result of the process, only small dimensions of a monolithic material can be produced. In the two-material system silicate-collagen the composition range in which monolithic xerogels can be produced is limited. The resulting structure can be affected exclusively by the respective component proportions of the silicate and of the collagen. Therefore, the material properties, and in this context primarily the mechanical properties, can be varied only within a narrow range.

German patent application DE 10 2004 012 411 A1 discloses composite materials on the basis of poly silicic acids and methods for their production, such composite material containing poly silicic acid, an organic polymer in a proportion of 0.1 to 20% by weight, at least one calcium phosphate phase with a proportion of more than 15% by weight and optionally an application-specific additive. In order to arrive at the disclosed composite materials, the individual components of the composite material, as a function of their chemical and physical properties, are combined sequentially or in combinations. Subsequently, the mixture is homogenized, brought into the desired shape, and then dried at temperatures of 100° C. and more.

German patent application DE 10 2006 014 522 A1 discloses a method for producing a bone replacement material in which a sol of an oxidic component that comprises as a solvent water and/or alcohol and has calcium phosphate phases homogeneously distributed therein is poured into a freezing mold that has been cooled to a temperature below the freezing point of the employed solvent. The solvent is frozen with gel formation and subsequently the frozen solvent is removed by freeze-drying so that an open-pore gel support structure with embedded calcium phosphate phases is produced.

In German patent application DE 198 11 600 A1 a biocompatible composite material is disclosed that contains an inorganic gel and, as a bioactive component, one or more homogeneously embedded scleroproteins and their hydrolysis products and/or glycosaminoglycans. By addition of calcium salts, phosphates or basic calcium phosphate suspension the bioactivity of the composite can be increased.

German patent application DE 199 62 090 A1 discloses shaped bodies having the geometry of bone or bone parts that are formed of collagen or mineralized collagen in the form of a dense network of collagen fibrils with or without an additional matrix of calcium phosphate cement in which the collagen fibrils are embedded and that are produced by a freeze drying method.

Many further methods disclosed in the prior art employ the sol-gel method. They are generally used only as a pre-stage and the obtained material is subsequently ground, pressed, and thermally treated. Because of the high temperatures of usually several hundred degrees Celsius, the powder sinters then to a monolith. Organic components are destroyed under these conditions.

The object of the invention is to develop a material system that, based on the starting components silicate and collagen, makes available further variation possibilities by means of which the solids contents of the hydrogel produced during the manufacturing process can be increased, a high bioactivity of the obtained composite material is to be achieved, and the structure and thus the mechanical properties of the composite material can be adjusted within a wide range.

A further object resides in that compact monolithic material systems are to be produced without thermal after treatment directly by means of a sol-gel process and to thereby, on the one hand, make available advantageously gentle methods in which the obtained collagen is not thermally destroyed but instead maintains its fiber structure and thus reinforces the composite material and, on the other hand, to keep low the energy expenditure required for producing the composite materials.

According to the invention the object is solved by a composite material comprising a collagen matrix that is mineralized with silicate and a calcium phosphate phase.

The collagen component of the composite material according to the invention can be in this connection recombinant collagen, collagen from Eumetazoa (i.e., eumatozoans, including Cnidaria and Bilateria), sponge collagen of the classes Demospongia (horn sponges) or Calcarea (calcareous sponges), a synthetic collagen analogue, a collagen derivative or a mixture of these collagens.

Collagen analogues are synthetically produced polypeptide chains whose primary sequence is designed such that they can simulate certain properties of native collagen monomers, for example, triple helix formation, fibrillogenesis, gel formation. Recombinant collagens are those whose primary sequence is identical to that of collagen type I. They are produced by means of genetically manipulated microorganisms and optionally further processed. Collagen derivatives are compounds that are derived formally from the basic component collagen and can be produced from it.

The second main component of bone, in addition to collagen, is calcium phosphate in the form of hydroxyl apatite. By introducing hydroxyl apatite and other calcium phosphate phases into the composite material according to the invention as an additional inorganic component that is introduced in powder form into the system, the solids proportion and the bioactivity of the composite material according to the invention are significantly increased. This is demonstrated, for example, by acceleration of formation of an hydroxyl apatite layer in vitro in simulated body fluid (SBF).

Depending on the composition of the calcium phosphate phases, different effects can be obtained in this connection. The structure is also affected which has an effect on the mechanical properties. All calcium phosphate compounds that enable a homogeneous mixture with the silicate solution and the collagen suspension are suitable.

Preferably, those calcium phosphate phases are used that in vivo are converted to hydroxyl apatite. In a preferred embodiment, as a calcium phosphate phase hydroxyl apatite ($Ca_{10}(PO_4)_6(OH)_2$), tricalcium phosphate ($Ca_3PO_4$), amorphous calcium phosphate ($Ca_x(PO_4)_y.nH_2O$), octacalcium phosphate ($Ca_8H_2(PO_4)_6.5H_2O$), or brushite ($CaHPO_4.2H_2O$) or mixtures of these calcium phosphate phases with each other, for example, calcium phosphate cement (a mixture of $Ca_3(PO_4)_2$, $CaCO_3$, $Ca(HCO_3)$ and $Ca_{10}(PO_4)_6(OH)_2$) or mixtures of or with calcium and phosphate salts such as $CaCl_2$ and/or $Na_2HPO_4$ are used. The calcium phosphate phase can be additionally doped with ions such as fluoride, silver, magnesium or carbonate.

In an especially preferred embodiment, as a calcium phosphate phase nanoscopic hydroxyl apatite ($Ca_{10}(PO_4)_6(OH)_2$) is used because it can be introduced especially homogeneously. A homogeneous distribution of the calcium phosphate phase in the material effects material properties that can be especially well reproduced. Nanoscopic hydroxyl apatite is comprised substantially of hydroxyl apatite nanoparticles that have preferably a size of 10 to 500 nm, preferably a size of less than 100 nm.

Collagen fibrils are configured of individual tropocollagen molecules in which three peptide chains combine to a triple helix of a length of approximately 300 nm. During fibrillogenesis the tropocollagen molecules aggregate to form larger collagen fibrils. By bundling of collagen fibrils by covalent transverse crosslinking, collagen fibers are formed in turn.

According to the composite materials of the present invention, as a collagen component any collagen can be used, i.e., collagen of any form (for example, fibrillar collagen, reticulate collagen, fiber-forming collagen, tropocollagen, partially or completely fibrillated collagen, partially or completely (irreversibly) denatured collagen, collagen fibers or larger aggregates etc.) and any type (for example, type I, II, III, IV, V, VI, VII, VIII, IX, X, XI, XII, XIII, XIV, XV, XVI, XVII, XVIII, XIX, XX, XXI, XXII, XXIII, XXIV, XXV, XXVI).

In the composite material according to the invention collagen is used preferably in the form of collagen fibrils or collagen fibers because, relative to pure silicate, it advantageously leads to significantly increase of the mechanical load capacity.

In an especially preferred embodiment, the organic component collagen is additionally biochemically modified. The modification of the collagen component is based in this connection on a targeted manipulation of the fibril geometry (diameter and length) by biochemical manipulations in the fibril genesis. Since the fibrils in the composite material take on the function of fiber reinforcement, their geometry has an effect on the mechanical properties of the composite material.

With the aid of aminosugar-containing polysaccharides, preferably glycosaminoglycans and their analogues, the fibril geometry can advantageously be affected in a targeted fashion. Compounds that are analogues to glycosaminoglycans are chemical compounds having the same biological effect. Especially preferred is in this connection the biochemical modification of the collagens by glycosaminoglycans chondroitin sulfate, dermatan sulfate, heparin, heparan sulfate, hyaluronic acid and keratan sulfate, but also by proteoglycans such as decorin and other aminosugar-containing polysaccharides like chitosan. [Wolf C, Hanke T., Scharnweber D., Peters K., Kirkpatrick C. J., Worch H.: Influence of artificial extracellular matrices on Ti6A14V implants on binding and release of VEGF, Abstracts International Symposium, Interface Biology of Implants', Rostock 14-16 May 2003, in: BIOmaterialien 4: 158, 2003; Wolf-Brandstetter C, Lode A., Hanke T., Scharnweber D., Worch H.: "Influence of Modified Extracellular Matrices on Ti6A14V implants on binding and release of VEGF". J. Biomed. Mat. Res A. 79: 882-894, 2006; Final Report "Innovative Materialsysteme für die Funktionalisierung von Implantaten und den Gewebeaufbau in der Implantologie" (Authors: Worch, H., Scharnweber, D., Hanke, T., 2002) BMBF Project 03N4015/9 (October 1999 to October 2002); Collection "Deutsche Forschungsberichte" TIB/UB Hannover].

The biochemical modification is realized by the incorporation of the aforementioned substances into the collagen matrix. The incorporation is preferably realized either by adsorptive immobilization or by covalent transverse crosslinking, for example, with N-(3-dimethyl amino propyl)-N'-ethical carbodiimide (EDC). The incorporation alternatively can also take place during spontaneous aggregation of the fibrils that is accomplished at neutral pH value (for example, in phosphate buffer or tris buffer) and at increased temperature of approximately 37° C. Subsequently, optionally a covalent crosslinking is carried out.

A composition of 40-92.5% silicate, 7.5-60% collagen, preferably 20-60% collagen, and up to 52.5% calcium phosphate, preferably up to 15% calcium phosphate, is preferred.

Compositions of 40-92.5% silicate, 7.5-30% collagen and up to 30% calcium phosphate have been found to be advantageous for the production of xerogels of the composite material according to the present invention. Especially preferred is a composition of 60-80% silicate, 10-20% collagen, and 10-20% calcium phosphate. Especially preferred is a composition of 65-80% silicate, 10-20% collagen, and 10-15% calcium phosphate.

For producing porous composite materials the collagen proportion is to be increased to approximately 50-90%.

An aspect of the invention is furthermore a method for producing a composite material of a collagen matrix that is mineralized with silicate and calcium phosphate phases and is optionally biochemically modified. The method is based on the sol-gel process. For this purpose, calcium phosphate phases are dissolved in a homogeneous collagen suspension. In the second step the silicate formation by addition of silicic acid in the form of a hydrolyzed silicon precursor is carried out wherein first a sol is formed.

Advantageously, by means of the introduction of collagen fibrils without any thermal after treatment a monolithic material can be obtained. In this way, on the one hand, the energy expenditure is minimized and, on the other hand, the final structure of the material can be adjusted in a targeted fashion by means of the organic component. In contrast to this, this possibility would not be available by thermal after treatment, by means of which the organic component is decomposed by the thermal action and is irreversibly destroyed.

The collagen concentration is advantageously to be selected as high as possible wherein the resulting suspension may not be too viscous in order to ensure processing and later miscibility. Preferred is a collagen concentration of 5-40 mg/ml especially preferred 20-25 mg/ml. As a collagen component of the composite material according to the invention any type of collagen can be used, i.e., collagen of any form (for example, fibrillar collagen, reticulate collagen, fiber-forming collagen, tropocollagen (individual collagen molecules), partially or completely fibrillated collagen, partially or completely (irreversibly) denatured collagen, collagen fibers or larger aggregates etc.) and any type (for example, type I, II, III, IV, V, VI, VII, VIII, IX, X, XI, XII, XIII, XIV, XV, XVI, XVII, XVIII, XIX, XX, XXI, XXII, XXIII, XXIV, XXV, XXVI). Preferred is collagen in the form of collagen fibrils or collagen fibers.

As a solvent of the collagen suspension in principle all solvents can be used that do not change the collagen in its necessary properties and moreover upon combination with the calcium phosphate component and the silicate component enable the aforementioned mineralization processes. The same holds true for the solution of the silicon precursor.

Preferably, the collagen is suspended in a solvent with neutral pH value, i.e., preferably at pH 6.5 to 7.5, preferably at pH 6.8 to 7.4, especially preferred at pH 7.0 to 7.2.

Advantageously, first the calcium phosphate phase in powder form is admixed to the homogenous collagen suspension. A homogenous admixture of the components is realized preferably by means of a vortex mixer, an impeller mixer, a magnetic stirrer, a static mixer or a vibration mill. Alternatively, the calcium phosphate can be dissolved prior to this in the buffer in which the collagen lyophilisate is suspended. In this connection, bonding of the calcium phosphate phase to the collagen takes place. As a calcium phosphate phase all calcium phosphate phases are useful that can be added in the form of a powder into the collagen suspension. In a preferred embodiment as a calcium phosphate phase hydroxyl apatite $(Ca_{10}(PO_4)_6(OH)_2)$, tricalcium phosphate $(Ca_3PO_4)$, amorphous calcium phosphate $(Ca_x(PO_4)_y \cdot nH_2O)$, octacalcium phosphate $(Ca_8H_2(PO_4)_6 \cdot 5H_2O)$, or brushite $(CaHPO_4 \cdot 2H_2O)$ or mixtures of these calcium phosphate phases with each other, for example, calcium phosphate cement (a mixture of $Ca_3(PO_4)_2$, $CaCO_3$, $Ca(HCO_3)$ and $Ca_{10}(PO_4)_6(OH)_2$) or mixtures of or with calcium and phosphate salts such as $CaCl_2$ and/or $Na_2HPO_4$ are used. The calcium phosphate phase can be additionally doped with ions such as fluoride, silver, magnesium or carbonate.

To the resulting collagen-calcium phosphate mixture, the silicic acid is added and admixed. In order to synthesize the silicic acid that is a prerequisite for all silicating reactions, according to the invention a silicon precursor is used. In a preferred embodiment of the composite material the silicon precursor is a hydrolyzed alkoxy silane solution $(Si(OR)_4$, $R=C_nH_{2n+1})$ or water glass, for example, $Na_2SiO_3$. In an especially preferred embodiment the alkoxy silane solution is a tetramethoxy silane (TMOS; $Si(OCH_3)_4$) solution or a tetraethoxy silane (TEMS; $Si(OC_2H_5)_4$) solution, preferably in molar ratio of TMOS:water or TEOS:water of 1:4.

The fibrils in the collagen suspension that has been enriched with the calcium phosphate phases serve as biological template and force the targeted polymerization of the silicic acid or of the silicate on the collagen fibrils. The seed formation is based on the attractive interactions between the positively charged amino groups of the collagen and the negatively charged oxide groups of the silicic acid or silicate particles. The collagen itself accelerates concentration-dependent the heterogeneous seed formation of the silicic acid polymerization on the fibrils. On the fibrils of the collagen, nanometer-sized silicate particles are formed, agglomerate thereon, and thus silicate them.

During polycondensation to silicate, the silicic acid crosslinks individual collagen molecules or fibrils with each other. During this transverse crosslinking calcium phosphate phases are embedded. As long as the gel point has not yet been reached, the mixture can be brought into any desired shape and in this way the final sample configuration can be determined. As a result of the polymerization of the silicic acid on the collagen fibrils (silication) and the crosslinking caused thereby of the collagen fibrils with each other the hydrogel is formed. In this way, as a function of the material proportions of the silicate, collagen and calcium phosphate, hydrogels can be generated.

In order to obtain a homogeneous hydrogel with defined composition, the gel formation should be terminated before the suspension begins to separate. In order to ensure that the gel formation can occur quickly, the collagen is preferably suspended in a solvent with neutral pH value.

The gel forming process then generally takes place within a few seconds. In this time period, a homogeneous intensive mixing of the components must be achieved. This is achieved preferably by means of a vortex mixer, an impeller mixer, a magnetic stirrer, a static mixer or a vibration mill. Should it be necessary with respect to process-technological aspects, the processing time, i.e. the time until the gel forms, can be extended in that the starting components are cooled to low temperatures (0-15° C.). With a minimal lowering of the pH value, preferably to pH 6.0 to 6.8, especially preferred pH 6.4 to 6.5, the processing time can be extended also. Subsequent to this, rinsing with neutral buffer is carried out after completed gel formation in order to reach again a neutral pH value of the material.

The obtained hydrogels can be converted by drying, preferably under special climatic conditions, into monolithic xerogels from the three-component composite material according to the present invention.

An aspect of the invention is therefore also a method for producing a hydrogel from collagen matrix that is mineralized with silicate and calcium phosphate phases in which first the calcium phosphate phase is dissolved in a homogenous collagen suspension and the collagen fibers are silicated in a second step by addition of silicic acid and in which the product subsequently, after reaching the gel point, is stored under exclusion of air for strengthening the solid body structure.

The hydrogels according to the invention can be converted by drying, preferably by drying in air, into a xerogel. An aspect of the invention is therefore also a method in which, for producing a xerogel, a hydrogel according to the invention is dried, preferably air-dried.

Advantageously, the hydrogels are first stored for at least 24 hours with exclusion of air. During this time, the gel network stabilizes.

The subsequent drying can be carried out at room climate or in a drying cabinet. Preferably, drying is carried out as slowly as possible in order to not surpass the gel stability. Preferably, for this purpose the gels are first kept at maximally 40° C., preferably at 37° C., and at a maximum relative humidity of 100%, preferably at 95% relative humidity, and successively room climate is generated, i.e., preferably a temperature of 20 to 25° C. and a relative humidity of 20-60%. The speed with which the temperature and relative humidity during the drying process are changed depends on the size of the hydrogel to be dried. Suitable drying conditions can be determined easily and quickly by a person of skill in the art by simple experiments.

In this way, monolithic xerogels can be produced. An aspect of the invention are also the xerogels that are obtained from the composite material according to the invention.

Alternatively, the hydrogel obtained from the composite material according to the invention can also be converted into an aerogel. For this purpose, the liquid phase is removed from the hydrogels such that no (or only minimal) capillary forces occur and therefore shrinkage of the material is avoided. Drying that is to be carried out under supercritical conditions requires first a substitution of the liquid phase of the hydrogels (for example, water and methanol when using TMOS as silicon precursor). For this purpose, the hydrogels are, for example, immersed for several days into ethanol of highest purity. The ethanol is exchanged regularly at identical intervals. Subsequently, critical point drying in an autoclave is performed. When doing so, the ethanol is first replaced with liquid carbon dioxide at a temperature of approximately 7° C. under high-pressure conditions by multiple flushing steps. Subsequently, the temperature is increased to 38 to 40° C. wherein the carbon dioxide passes into the supercritical state, i.e., there is no boundary surface between liquid and gaseous phases. By a valve the supercritical carbon dioxide is slowly released while maintaining the conditions. By avoiding the boundary surfaces no capillary forces can be generated and the solid body structure of the sample remains unchanged. After completion of this process, dried aerogels are obtained whose inner and outer structures correspond to those of the employed hydrogels.

An aspect of the invention is therefore also an aerogel that is obtainable by substitution of the liquid phase of a hydrogel according to the invention and subsequent drying under supercritical conditions.

An aspect of the invention is moreover a method for producing an aerogel in which the liquid phase of a hydrogel according to the invention is substituted and subsequently drying under supercritical conditions is performed.

Based on the method according to the invention, by freeze drying it is also possible to produce, instead of gels, porous collagens scaffolds that are mineralized with silicate and calcium phosphate. For this purpose, first a calcium phosphate phase is dissolved in a homogeneous collagen suspension. Depending on the employed collagen, the collagen concentration can be increased in this connection as long as the obtained suspension can still be homogeneously mixed with the silicate component (pre-hydrolyzed alkoxy silane solution). In order to obtain the character of a porous collagen scaffold, and not that of a silicate gel, collagen proportions of approximately 50-90% are advantageously preferred.

An aspect of the invention is therefore also a method in which for producing a porous collagen scaffold that is mineralized with silicate and a calcium phosphate phase, a calcium phosphate phase is first dissolved in a homogeneous collagen suspension and the product is mixed with a minimal quantity of a hydrolyzed alkoxy silane solution and subsequently freeze drying is performed.

An aspect of the invention is therefore also a porous collagen scaffold that is mineralized with silicate and a calcium phosphate phase and is obtainable by freeze drying of a composite material according to the invention.

Moreover, the method according to the invention is suitable for producing composite particles. Composite particles are obtainable in that a homogeneous collagen suspension that is enriched with calcium phosphate is added to an alkoxy silane solution. For producing spherical particles, first the calcium phosphate phase is dissolved in a homogeneous collagen suspension and the appropriate concentrated solution is pipetted dropwise into a pure alkoxy silane solution. Upon dropwise addition of the collagen suspension, of neutral pH value (for example, tris/HCl buffer) and with added calcium phosphate phase to the alkoxy silane solution, a local hydrolysis by the availability of water and the template function of the collagen leads to spontaneous polymerization of the silicic acid resulting in a spherical composite particle. This sphere is removed after approximately 24 hours from the solution, rinsed and air-dried. The resulting product corresponds thus to a spherically shaped composite xerogel.

Aspects of the invention are therefore a method in which for producing particles first the calcium phosphate phase is dissolved or suspended in a homogeneous collagen suspension and the solution is subsequently added to an alkoxy silane solution, as well as particles of the composite materials according to the invention.

As a particle the composite material according to the invention is suitable, for example, as an active ingredient carrier ("drug delivery system"). Aspect of the invention is therefore also the use of the particle as an active ingredient carrier.

The composite material according to the invention is suitable moreover for coating a suitable substrate, for example, Ti6Al4V. For producing such a coating, first a calcium phosphate phase is dissolved or suspended in a homogeneous collagen suspension and the solution is subsequently mixed with an alkoxy silane solution. The concentration of the collagen suspension and the alkoxy silane solution are selected to be so low that the mixed solution will not reach the gel point in the experimental time frame. For coating, the substrates (for example, biocompatible metallic plates) are immersed in the mixed solution and slowly pulled out. As this is done, a layer is deposited on the substrates whose thickness and properties are primarily determined by the composition of the mixed solution and the removal speed. The layers dry in air to a dense and mechanically stable substrate coating.

An aspect of the invention is therefore also a coating material of a composite material according to the invention as well as a method in which, for coating a substrate with a composite material, a calcium phosphate phase is first dissolved or suspended in a homogeneous collagen suspension, the solution is then mixed with a silicic acid precursor, and the substrate is immersed in the mixed solution and subsequently dried.

An aspect of the invention is also the use of this coating for biologizing implant surfaces. Biologizing coating is understood as finishing a substrate with a biologically effective and/or bioactive substance.

The invention is based on the surprising scientific finding that in the three-material system collagen-silicate-calcium phosphate under defined conditions macroscopic composite materials can be produced whose biological and mechanical properties can be varied in a wide range. This enables a targeted adjustment of the material properties to the site of use in a way that has not been possible up to now.

The composite material according to the invention of a collagen matrix that is mineralized with silicate and calcium phosphate is biocompatible, bioactive, and can withstand even higher mechanical loads.

By a targeted biochemical modification of the fibril geometry the mechanical properties of the composite materials according to the invention can be affected. By the biochemical modification by means of aminosugar-containing polysaccharides such as glycosaminoglycans, for example, chondroitin sulfate, dermatan sulfate, heparin, heparan sulfate, or chitosan and/or proteoglycans (decorin), the geometry of the collagen fibrils can be affected in a targeted fashion. An aspect of the invention is therefore also a method in which the collagen, before mixing with calcium phosphate phases and silication by the silicon precursor, is first modified by aminosugar-containing polysaccharides, preferably glycosaminoglycans.

The composite material according to the invention of a twice mineralized and optionally biochemically modified collagen matrix is moreover structurally and materially variable in wide ranges and is thus suitable for producing multifaceted applications with mechanical and biologically adjusted properties. By using the sol-gel technology and because of the mechanical load capacity, the material can be produced in different geometric forms.

The material composition can be varied within the entire three-material system (see FIG. 1). Preferred is a composition of 40-92.5% silicate, 7.5-60% collagen, and up to 52.5% calcium phosphate (FIG. 1, areas marked in gray). It has been found that compositions of 40-92.5% silicate, 7.5-30% collagen, and calcium phosphate (FIG. 1, areas marked in dark gray) are advantageous for the production of xerogels of the composite material according to the invention.

The composite materials according to the invention are in principle suitable for technical and biological purposes. They can be used as construction material and/or functional material. They are suitable as implant material in biomedicine where, in addition to good biocompatibility, a satisfactory strength (for example, in bone contact) is required. They are preferably used as implant material in unloaded but also load-bearing areas. The applications range from simple defect filling (mandible area, skull area) to the point of taking over functions of the material, for example, as a pin for fixation of fractures or ligaments. Because of the advantageous manipulation of the mechanical properties of the composite materials according to the invention as well as their high bioactivity, they are suitable for a large number of application possibilities. They can be molded into shaped pieces but can also be used for a biologizing coating of implants of other materials. For this purpose, the substrate to be coated is immersed in the composite material as long as the gel point has not yet been reached and subsequently dried.

A further field of application is "loading" of the composite materials with pharmaceutically active ingredients. This can be used, on the one hand, for producing administration systems with delayed release. Alternatively, implants can be loaded for example with bioactive ingredients (factors) that trigger in a targeted fashion useful cell reactions. In particular in bone contact the ratio of osteoclast-osteoblast activity can be affected in this way. Preferably, bisphosphonates are used for this purpose.

BRIEF DESCRIPTION OF THE DRAWINGS

Based on the following Figures and embodiments the invention will be explained in more detail without being limiting.

PREFERRED EMBODIMENTS OF THE INVENTION

Embodiment 1

Cylindrical Samples of the Composite Material of Silicate, Calf Skin Collagen, and Hydroxyl Apatite Lyophilisate of calf skin collagen is suspended in neutral tris/HCl buffer (100 mmol, pH 7.4) for 24 hours with stirring so that a concentration of 20 mg/ml results. Hydroxyl apatite ($Ca_{10}(PO_4)_6(OH)_2$) is then added in powder form into the collagen suspension and dissolved over 24 hours with stirring. Alternatively, the calcium phosphate can be dissolved prior to this in the buffer in which later the collagen lyophilisate is suspended. The weighed quantity of calcium phosphate phases to be added as well as the corresponding volumes of silicic acid and collagen suspension depends on the desired composition. In this embodiment, a mass composition of 70% silicate, 15% collagen, and 15% calcium phosphate is listed.

For generating silicic acid, tetraethoxy silane (TEOS, 99%, Sigma) is hydrolyzed by addition of water and hydrochloric acid (10 mmol) as catalyst at 4° C. for 24 hours. The molar ratio of tetraethoxy silane to water is 1:4. This solution serves as the silicate component and is supplied to the collagen suspension that is enriched with calcium phosphate and is mixed intensively. After a few minutes a hydrogel is formed.

The employed volumes per sample and the mold into which the mixtures are introduced determine the finally obtained geometry of the xerogel. A volume of 500 μl and cylindrical vessels of 14 mm diameter result in disk-shaped xerogels of 5 mm diameter and 2 mm height. A volume of 3,500 μl at 15 mm diameter results in cylindrical xerogels of approximately 11 mm diameter and 16 mm height.

Figure 1:
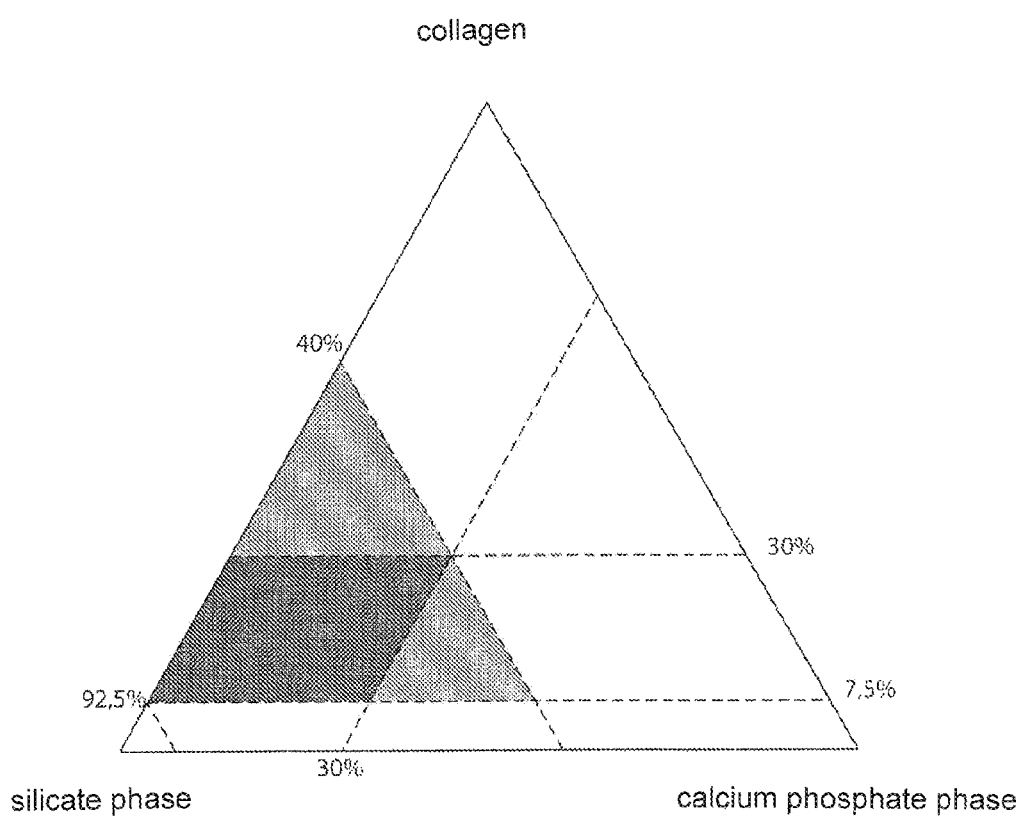
FIG. 1 shows preferred compositions of the three-material system according to the invention.
Figure 2:
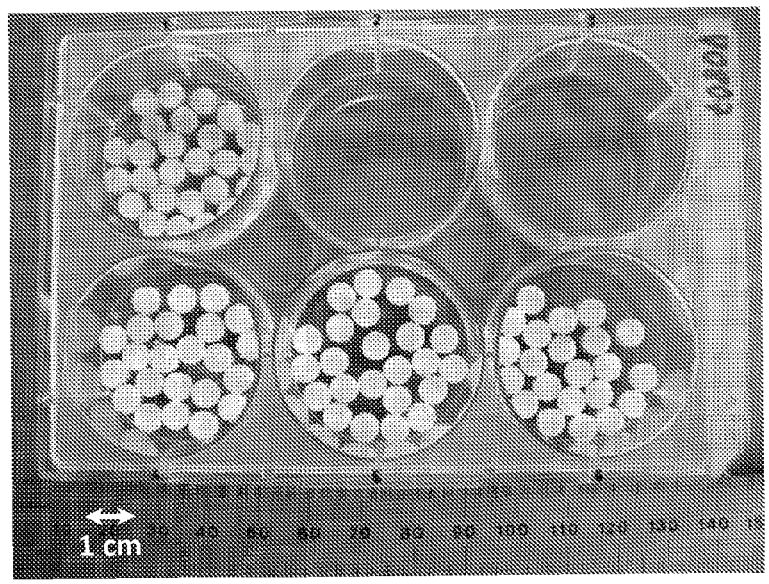
FIG. 2 shows the thus obtained disk-shaped (FIG. 2a) and cylindrical (FIG. 2b) xerogels.
Figure 2:
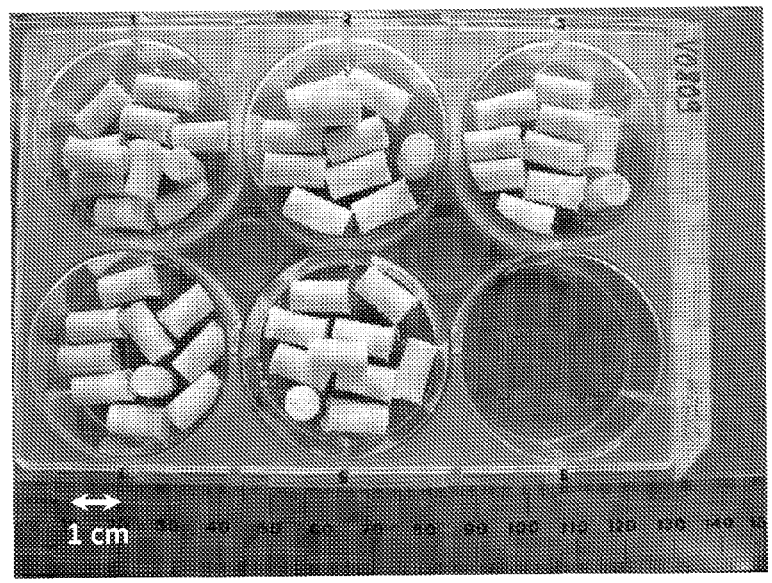

The hydrogels are stabilized under exclusion of air for 24 hours at room temperature. Drying to xerogels is realized with open vessels at 37° C. and 95% relative humidity. After 7 days, the climate is continuously regulated over 24 hours to 20° C. and 30 relative humidity. For a composition of 85% silicate, 15% collagen or 70% silicate, 15% collagen, 15% calcium phosphate, FIG. 2 shows the obtained disk-shaped (FIG. 2a, upper row: 85% silicate, 15% collagen; lower row three-material systems 70% silicate, 15% collagen, and 15% calcium phosphate, from left to right: calcium phosphate cement, hydroxyl apatite, amorphous calcium phosphate) and cylindrical (FIG. 2b, upper row, left: 85% silicate, 15% collagen; center: three-material system with calcium phosphate cement; right: three-material system with hydroxyl apatite; lower row three-material system showing to the right: amorphous calcium phosphate, center: salt mixture) xerogels. The cylindrical xerogels are machined by cutting on a conventional lathe.

Embodiment 2

Characterization of Bioactivity of the Xerogels

Figure 3:
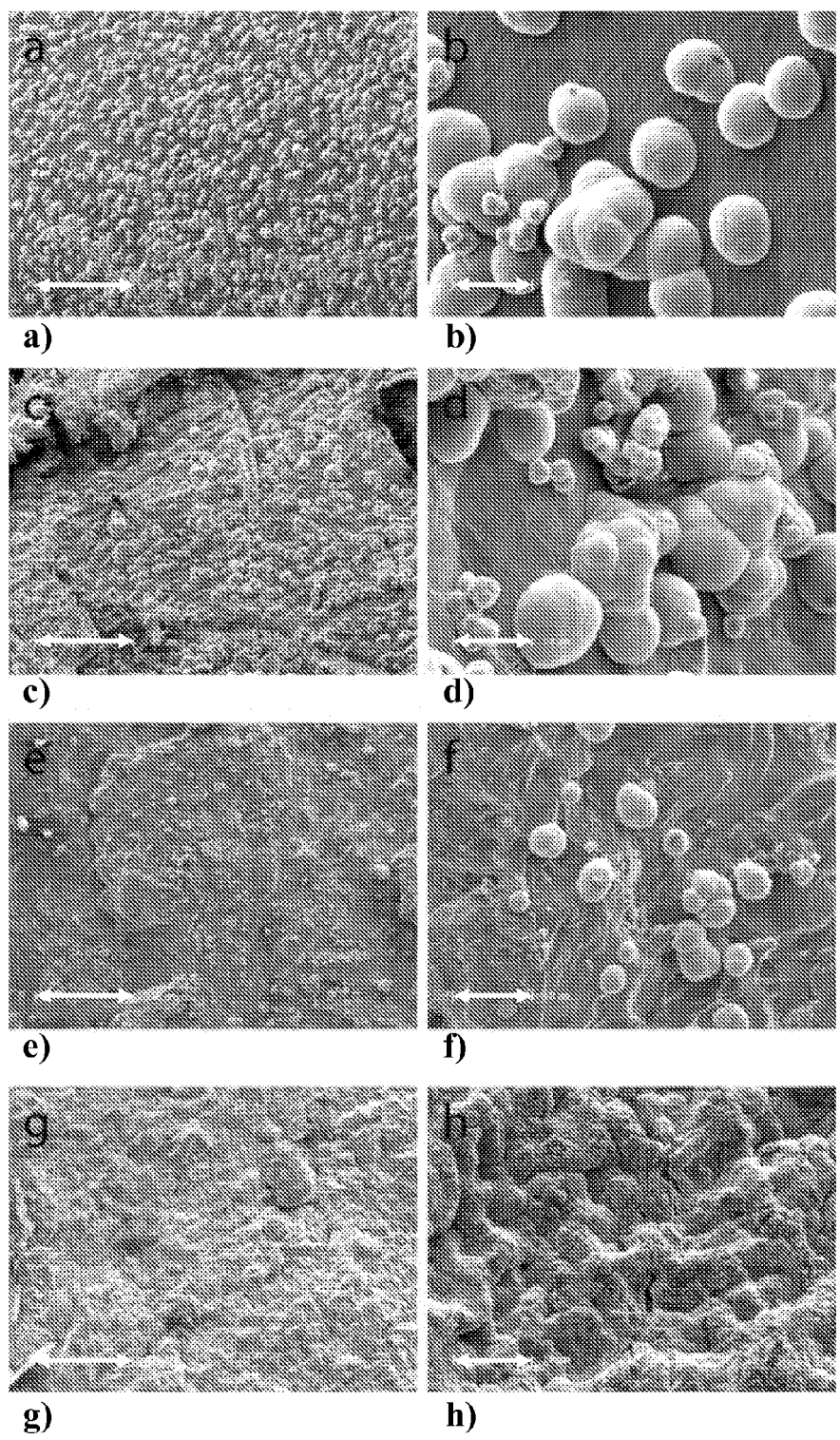
FIG. 3 shows scanning electron microscope images of composite materials of 100% silicate (a, b); 85% silicate, 15% collagen (c, d); 70% silicate, 30% collagen (e, f); 70% silicate, 15% collagen, 15% calcium phosphate cement (g, h) in two different resolutions wherein the superimposed white bar indicates a length of 100 μm (FIGS. 3, a, c, e, and g) or 10 μm (FIGS. 3, b, d, f, and h).

The disk-shaped xerogels of the composite material obtained as described in Embodiment 1 are stored in simulated body fluid (SBF). After 7 days the samples are removed and examined by means of scanning electron microscope. FIG. 3 shows images of composite materials of 100% silicate (FIGS. 3a, b); 85% silicate, 15% collagen (FIGS. 3c, d); 70% silicate, 30% collagen (FIGS. 3e, f); 70% silicate, 15% collagen, 15% calcium phosphate cement (FIGS. 3g, h).

The superimposed scale bar correspond to a length of 100 μm (FIGS. 3a, c, e, and g) or 10 μm (FIGS. 3b, d, f, and h).

The hydroxyl apatite that is formed in vitro can be seen as an insular shape on the surface. The images show that based on pure silicate the bioactivity with increasing collagen proportion decreases slightly, i.e., the density of the formed hydroxyl apatite islands decreases. On the other hand, for the three-material system according to the invention with calcium phosphate cement (FIGS. 3g, h) a strongly increased in vitro bioactivity is found, i.e., a closed apatite layer has formed that covers the entire mineralized collagen matrix. The higher resolution (FIG. 3h) shows that the apatite crystals are smaller than in the comparative examples that do not contain calcium phosphate cement (FIGS. 3b, d, and f).

Embodiment 3

Comparison of Different Calcium Phosphate Phases in the Composite Material

Figure 4:
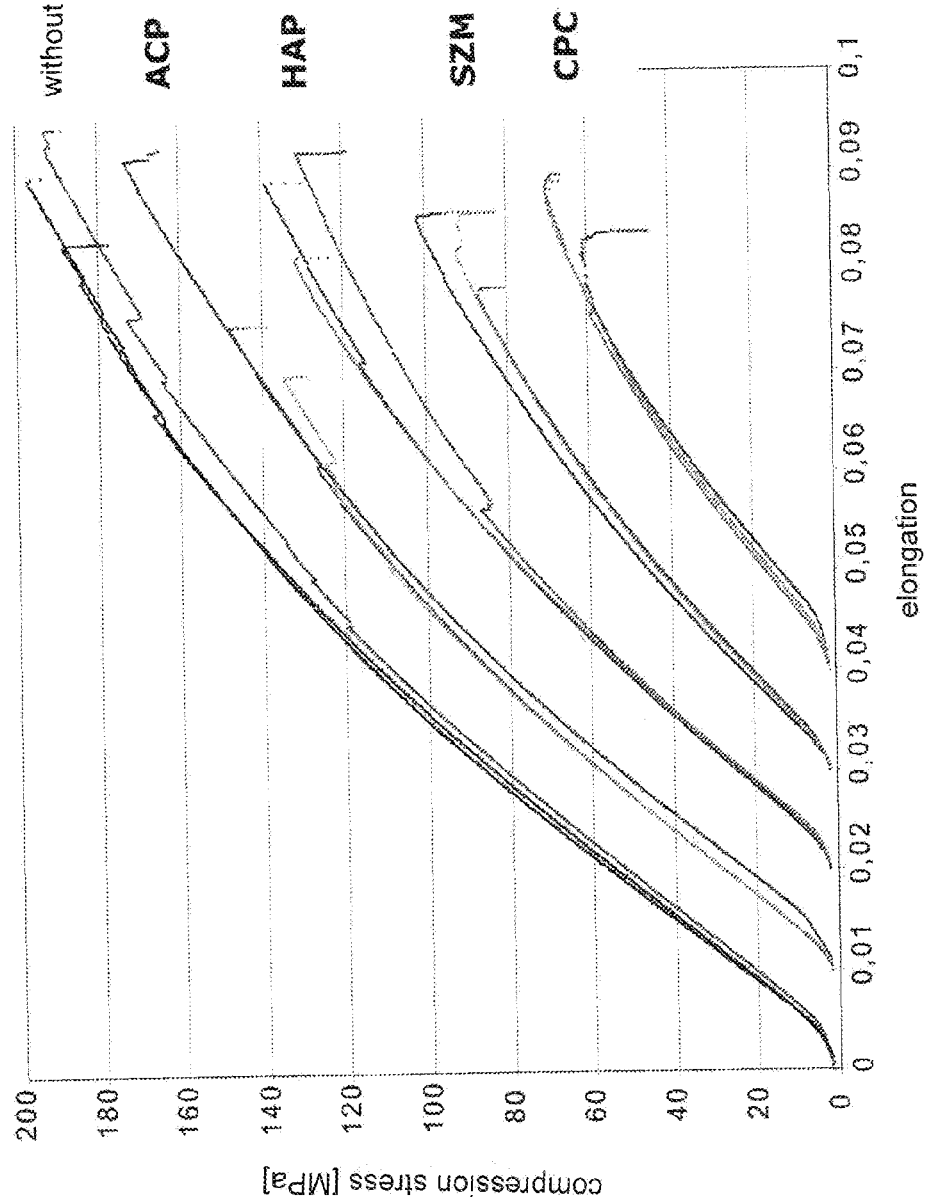
FIG. 4 shows the dependency of compression strength of the composite material as a function of the employed calcium phosphate phase.

The sample production is carried out in analogy to Embodiment 1. As calcium phosphate phase, in addition to hydroxyl apatite (HAP), calcium phosphate cement (CPC; a mixture of $Ca_3(PO_4)_2$, $CaCO_3$, $Ca(HCO_3)$ and $Ca_{10}(PO_4)_6(OH)_2$), amorphous calcium phosphate (ACP; $Ca_x(PO_4)_y \cdot nH_2O$) and a salt mixture (SZM, comprised of $CaCl_2$, $Na_2HPO_4$) are also used. As a comparative sample the two-component system of 85% silicate and 15% collagen is used. Cylindrical samples are produced and tested by means of compression experiments with respect to mechanical properties. FIG. 4 shows how the compression strength of the composite material changes as a function of the employed calcium phosphate phase. In this way, the properties of the composite material can be adapted to the site of use.

What is claimed is:

1. A method for producing a composite material comprising a collagen matrix mineralized with silicate and a calcium phosphate phase, the method comprising:
    a) suspending collagen in a solvent with a pH of 6.5 to 7.5 to a homogeneous collagen suspension and dissolving a calcium phosphate phase in the homogeneous collagen suspension, wherein the collagen suspension contains 5 mg/ml collagen to 40 mg/ml collagen;
    b) combining silicic acid in the form of a silicon precursor with the product of step a).

2. The method according to claim 1, wherein the silicon precursor is a hydrolyzed alkoxy silane solution or water glass.

3. The method according to claim 2, wherein the alkoxy silane solution is tetramethoxy silane (TMOS) solution or tetraethoxy silane (TEOS) solution.

4. The method according to claim 1, wherein, to produce a hydrogel of the composite material, in the step b) the silicon precursor is a hydrolyzed alkoxy silane solution that is mixed with the product of step a) to a mixture and, after the mixture has reached a gel point, the mixture is stored for strengthening a solid body structure in a suitable solvent with exclusion of air.

5. The method according to claim 4, comprising the step of drying the hydrogel to produce a xerogel.

6. The method according to claim 5, comprising the steps of replacing a liquid phase of the hydrogel and subsequently drying the hydrogel under supercritical conditions to produce an aerogel of the composite material.

7. The method according to claim 1, wherein, to produce a silicated porous collagen scaffold of the composite material, in the step b) the silicon precursor is a hydrolyzed alkoxy silane solution that is mixed in minimal quantities with the product of step a) to produce a mixture and subsequently the mixture is freeze dried.

8. The method according to claim 1, wherein, to produce particles of the composite material, the product of step a) is added to the silicon precursor that is an alkoxy silane solution.

9. The method according to claim 1, further comprising the steps of immersing a substrate into the combined product of step b) and drying the substrate after removal of the substrate from the combined product to produce a coating of the composite material on the substrate.

10. The method according to claim 1, wherein the collagen suspension contains 20 mg/ml collagen to 40 mg/ml collagen.

* * * * *